(12) United States Patent
Dutta et al.

(10) Patent No.: US 6,506,202 B1
(45) Date of Patent: Jan. 14, 2003

(54) EXPANDABLE STENT DIMENSIONAL RETENTION SYSTEM AND METHOD

(75) Inventors: Debashis Dutta, Santa Clara, CA (US); Chicheng Wang, Sunnyvale, CA (US)

(73) Assignee: Advanced Cardiovascular Systems, Inc., CA (US)

(*) Notice: Subject to any disclaimer, the term of this patent is extended or adjusted under 35 U.S.C. 154(b) by 244 days.

(21) Appl. No.: 09/612,855

(22) Filed: Jul. 10, 2000

(51) Int. Cl.[7] .................................. A61M 29/00
(52) U.S. Cl. ............ 606/194; 604/103.05; 604/103.06; 604/103.08
(58) Field of Search .................. 606/194; 604/96.01, 604/103.05, 103.06, 103.07, 103.08, 264; 428/35.2, 35.5, 36.91, 36.92

(56) References Cited

U.S. PATENT DOCUMENTS

| | | |
|---|---|---|
| 5,037,392 A | 8/1991 | Hillstead |
| 5,059,169 A | 10/1991 | Zilber |
| 5,064,435 A | 11/1991 | Porter |
| 5,116,318 A | 5/1992 | Hillstead |
| 5,226,889 A | 7/1993 | Sheiban |
| 5,409,495 A | 4/1995 | Osborn |
| 5,476,476 A | 12/1995 | Hillstead |
| 5,478,320 A * | 12/1995 | Trotta ................. 604/103.06 |
| 5,620,649 A * | 4/1997 | Trotta ................. 604/103.06 |
| 5,645,559 A | 7/1997 | Hachtman et al. |
| 5,653,691 A | 8/1997 | Rupp et al. |
| 5,667,523 A | 9/1997 | Bynon et al. |
| 5,695,498 A | 12/1997 | Tower |
| 5,746,745 A | 5/1998 | Abele et al. |
| 5,769,817 A * | 6/1998 | Burgmeier ........... 604/103.06 |
| 6,010,480 A * | 1/2000 | Abele et al. .......... 604/103.06 |
| 6,217,586 B1 | 4/2001 | Mackenzie |
| 6,221,043 B1 * | 4/2001 | Fischell et al. ...... 604/103.07 |
| 6,242,063 B1 * | 6/2001 | Ferrera et al. ............ 428/35.2 |
| 6,245,076 B1 | 6/2001 | Yan |
| 6,258,099 B1 | 7/2001 | Mareiro et al. |
| 6,248,333 B1 * | 9/2001 | Wang et al. .............. 428/35.5 |

* cited by examiner

Primary Examiner—Teresa Walberg
Assistant Examiner—Fadi H. Dahbour
(74) Attorney, Agent, or Firm—Fulwider Patton Lee & Utecht, LLP

(57) ABSTRACT

A system used in a blood vessel when an interventional procedure is being performed in a stenosed or occluded region, which is capable of treating an entire affected area in a blood vessel while preventing adverse effects for healthy tissue. The system includes a catheter which is positionable in a blood vessel at the interventional procedure site. The system further includes an expandable interventional instrument such as an expandable stent which is expandable and which may be deployed in the blood vessel at the interventional procedure site, which includes an unexpanded axial dimension. The system also includes an expandable member such as an expandable balloon, for expanding the expandable stent. The expandable balloon is capable of expanding so as to expand and deploy the expandable stent, and to substantially retain the unexpanded axial dimension of the expandable stent. The expansion of the expandable balloon prevents lengthening or shortening of the expandable stent, so as to enable the entire affected lesion area to be covered precisely without affecting the surrounding healthy tissue upon deployment of the expandable stent.

28 Claims, 3 Drawing Sheets

EXPANDABLE STENT DIMENSIONAL RETENTION SYSTEM AND METHOD

BACKGROUND OF THE INVENTION

The present invention relates generally to a system which can be used when an interventional procedure is being performed in a stenosed or occluded region of a blood vessel to substantially retain the unexpanded axial dimension of an expandable interventional instrument upon expansion thereof. The system of the present invention is particularly useful when performing stenting procedures in critical vessels, such as the carotid arteries.

A variety of non-surgical interventional procedures have been developed over the years for opening stenosed or occluded blood vessels in a patient caused by the build up of plaque or other substances on the walls of the blood vessel. Such procedures usually involve the percutaneous introduction of the interventional device into the lumen of the artery, usually through a catheter. One widely known and medically accepted procedure is balloon angioplasty in which an inflatable balloon is introduced within the stenosed region of the blood vessel to dilate the occluded vessel. The balloon catheter is initially inserted into the patient's arterial system and is advanced and manipulated into the area of stenosis in the artery. The balloon is inflated to compress the plaque and press the vessel wall radially outward to increase the diameter of the blood vessel.

Another procedure is laser angioplasty which utilizes a laser to ablate the stenosis by super heating and vaporizing the deposited plaque. Atherectomy is yet another method of treating a stenosed blood vessel in which a cutting blade is rotated to shave the deposited plaque from the arterial wall. A vacuum catheter is usually used to capture the shaved plaque or thrombus from the blood stream during this procedure.

In another widely practiced procedure, the stenosis can be treated by placing an expandable interventional instrument such as an expandable stent into the stenosed region to hold open and sometimes expand the segment of blood vessel or other arterial lumen. Stents are particularly useful in the treatment or repair of blood vessels after a stenosis has been compressed by percutaneous transluminal coronary angioplasty (PTCA), percutaneous transluminal angioplasty (PTA) or removal by atherectomy or other means. Stents are usually delivered in a compressed condition to the target site, and then are deployed at the target location into an expanded condition to support the vessel and help maintain it in an open position.

Prior art stents typically fall into two general categories of construction. The first type of stent is expandable upon application of a controlled force, often through the inflation of an expandable member such as an expandable balloon in a dilatation catheter which, upon inflation of the balloon or other expansion means, expands the compressed stent to a larger diameter to be left in place within the artery at the target site. The second type of stent is a self-expanding stent formed from, for example, shape memory metals or superelastic nickel-titanum (NiTi) alloys, which will automatically expand from a compressed state when the stent is advanced out of the distal end of the delivery catheter into the body lumen. Such stents manufactured from expandable heat sensitive materials allow for phase transformations of the material to occur, resulting in the expansion and contraction of the stent.

Stent delivery systems typically include a balloon catheter, a stent which is mounted on the balloon, and a delivery sheath which surrounds the stent-delivery catheter. Initial angioplastic dilation of the lesion produces a residual lumen large enough to accept the stent delivery system. The guiding catheter used to perform the initial dilation is typically left in place in the patient and reused during the stent implantation procedure. The stent-delivery catheter is routed through the guiding catheter to a position in which its distal end is disposed substantially coextensively with the distal end of the guiding catheter and immediately proximate of previously expanded lesion.

Once properly positioned relative to the guiding catheter, the stent-carrying catheter is extended from the distal end of the gliding catheter until the stent spans the previously dilated lesion. The delivery sheath which is slidable relative to the delivery catheter, balloon and stent, is then withdrawn into the guiding catheter to expose the balloon and stent. The delivery catheter is then supplied with a pressurized fluid, which expands the balloon and associated stent to a desired diameter sufficient to exceed the elastic limit of the stent. The stent thus comes in contact with, and permanently supports, the wall of the vessel. The delivery catheter balloon is then deflated and the delivery catheter and guiding catheter are withdrawn, leaving the expanded stent supporting the vessel lumen.

The above stent delivery procedure, if successful, avoids the necessity of major surgical operations. It is desirable to position the undeployed stent near the middle of the length of the affected area, such that upon radial expansion for deployment thereof, it will be positioned so as to precisely treat the entire affected area. However, for balloon-expandable stents, the expansion characteristics of the balloon may result in changes in the unexpanded axial dimension of the stent, constituting the unexpanded length thereof, upon radial expansion, which may cause stent lengthening or shortening from the initial length of the stent in its unexpanded condition. Stent lengthening may adversely affect healthy tissue, while stent shortening may fail to treat the entire affected area. Stent shortening may result from inadequate adhesion between the stent and the balloon as the balloon is being inflated. When a balloon is inflated, it grows axially. However, a stent crimped on the balloon usually shortens as the balloon inflates. This contradictory phenomenon of axial balloon growth and stent shortening may occur due to the loss of friction contact between the stent and the balloon during deployment. Stent shortening may still occur even when the stent is crimped with a heat and pressure process, which improves stent retention through mechanical interlocks formed between the balloon and stent. This process does not always, however, prevent the stent from decoupling during deployment.

The above problems may arise from the expansion characteristics of the expandable balloon used to expand and deploy the stent. The expandable balloon may be manufactured from a single layer of material such as polyurethane, having strong adhesion characteristics such that balloon axial growth may cause the stent to grow beyond its stated length, which could adversely affect healthy tissue extending beyond the affected area. Further, a condition known as "dog boning" may arise whereby the ends of the expandable balloon may expand initially while the middle portion of the stent remains unexpanded. As the ends of the balloon expand, they may tend to push the struts of the stent inward causing shortening of the stent and preventing treatment to the entire affected area.

What has been needed is a reliable system and method for delivering an expandable interventional device for treating stenosis in blood vessels which treat precisely the length of the lesion constituting the entire affected area, and which do not adversely affect surrounding healthy tissue. The system and method should be capable of expanding the expandable interventional device while retaining the unexpanded length thereof to allow the precise placement of the stent over the lesion to be treated. The system and method should be relatively easy for a physician to use. Moreover, such a system should be relatively easy to deploy and remove from the patient's vasculature. The inventions disclosed herein satisfy these and other needs.

SUMMARY OF INVENTION

The present invention provides a system and method for treating an entire affected area in a blood vessel during the performance of a therapeutic interventional procedure, such as a balloon angioplasty or stenting procedure, while preventing adverse effects to surrounding tissue. The present invention is particularly useful when performing an interventional procedure in vital arteries, such as the carotid arteries, including the main blood vessels leading to the brain or other vital organs. As a result, the present invention provides the physician with a higher degree of confidence that an entire lesion will be treated, and that healthy tissue will not be adversely affected by the stenting procedure.

The present invention enables an interventional procedure to be performed in a blood vessel at an interventional procedure site, such that the unexpanded axial dimension of an expandable interventional instrument is substantially retained upon expansion of the expandable interventional instrument.

In the present invention, the system includes a catheter for positioning in a blood vessel at an interventional procedure site, an expandable interventional device located at a distal end portion of the catheter for expanding and deploying in the blood vessel at the interventional procedure site, which includes an unexpanded axial dimension, and an expandable member for expanding the expandable interventional instrument so as to substantially retain the unexpanded axial dimension of the expandable interventional instrument and the expandable member.

In an embodiment of the present invention, the system includes a catheter, including an elongated shaft having a distal end portion adapted to be positioned in a blood vessel at an interventional procedure site. An expandable interventional device, such as an expandable stent, is adapted to be located in the distal end portion of the catheter shaft, and to be expanded and deployed in the blood vessel at the interventional procedure site, which expandable stent includes an unexpanded axial dimension, and is adapted to be expandable in a direction generally transverse to the axial dimension thereof. An expandable member, such as an expandable balloon, for expanding the expandable interventional instrument includes an unexpanded axial dimension, and is adapted to be located in the distal end portion of the catheter shaft, to be expandable within the blood vessel at the interventional procedure site in a direction generally transverse to the axial dimension thereof. The expandable balloon is further adapted to increase the adhesion between the expandable balloon and the expandable stent such that the expandable balloon substantially adheres to the expandable stent during deployment of the expandable stent, and to substantially retain the unexpanded axial dimension of the expandable member and the expandable stent upon expansion thereof. The expandable balloon is in fluid communication with an inflation lumen. Upon inflation with a suitable fluid, the expandable balloon expands the expandable stent so that the expandable stent is deployed within the blood vessel at the interventional procedure site, with the unexpanded axial dimension thereof substantially retained. The substantially retained unexpanded axial dimension of the deployed expandable stent enables the entire affected area to be treated, while preventing adverse effects for the healthy tissue.

In a particular embodiment of the present invention, the expandable balloon is comprised of a plurality of layers, wherein one of the plurality of layers is comprised of a material which has a substantially high coefficient of friction, and which is adapted to substantially adhere to the expandable stent during the deployment of the expandable stent, and another of the plurality of layers is comprised of a material which has a substantially low axial growth, and which is adapted to substantially retain the unexpanded axial dimension of the expandable stent upon expansion thereof, so as to enable the expandable stent to pin, contact, and compress the entire area to be treated, while not affecting healthy tissue.

In another particular embodiment of the present invention, the expandable balloon is comprised of a layer, which is comprised of a material which has a substantially low axial growth, and which is adapted to substantially retain the unexpanded axial dimension of the expandable stent upon expansion thereof, and a coating, comprised of a material which has a substantially high coefficient of friction, and which is adapted to substantially cover the layer and to substantially adhere to the expandable stent during deployment of the expandable stent, for enabling the expandable stent to treat the entire affected area, without adversely affecting surrounding healthy tissue.

Other features and advantages of the present invention will become more apparent from the following detailed description of the preferred embodiments of the invention, when taken in conjunction with the accompanying exemplary drawings.

DETAILED DESCRIPTION OF THE PREFERRED EMBODIMENTS

The present invention is directed to an improved system and method for efficiently and effectively enabling an interventional procedure to be performed in a blood vessel at an interventional procedure site. The preferred embodiments of the improved system and method are illustrated and described herein by way of example only and not by way of limitation. While the present invention is described in detail as applied to the carotid arteries of the patient, and the disclosed interventional procedure is directed to a stenting procedure, those skilled in the art will appreciate that it can also be used in other body lumens as well, such as the coronary arteries, renal arteries, saphenous veins and other peripheral arteries. Additionally, the present invention can be utilized when performing any one of a number of interventional procedures, such as balloon angioplasty, laser angioplasty or atherectomy.

Figure 1:
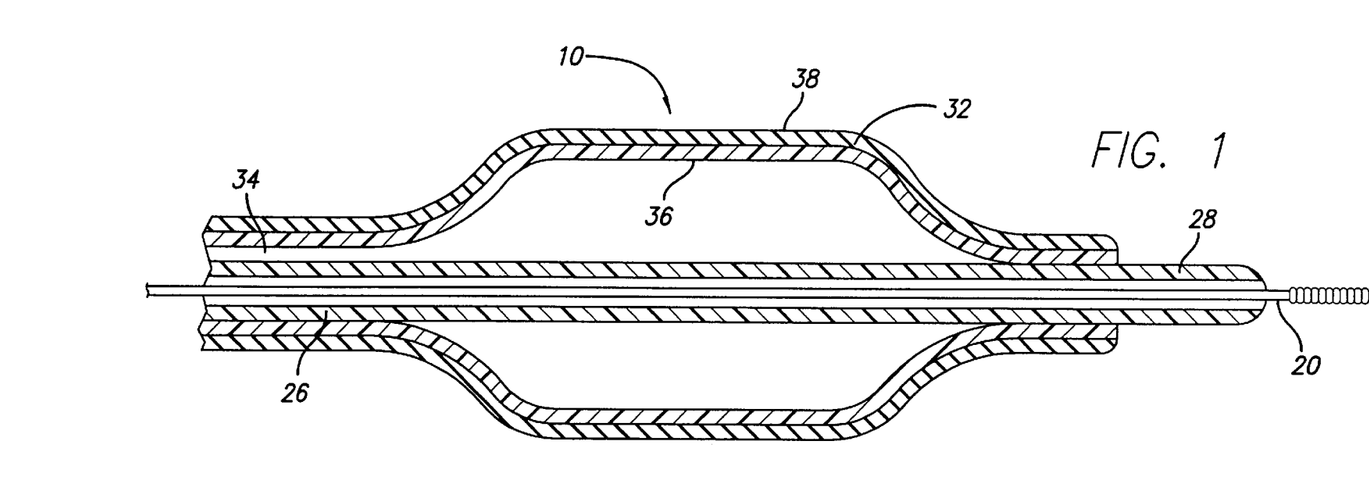
FIG. 1 is an elevational view, partially in section, depicting the system of the present invention, including a catheter and a first embodiment of an expandable member in expanded condition.
Figure 2:
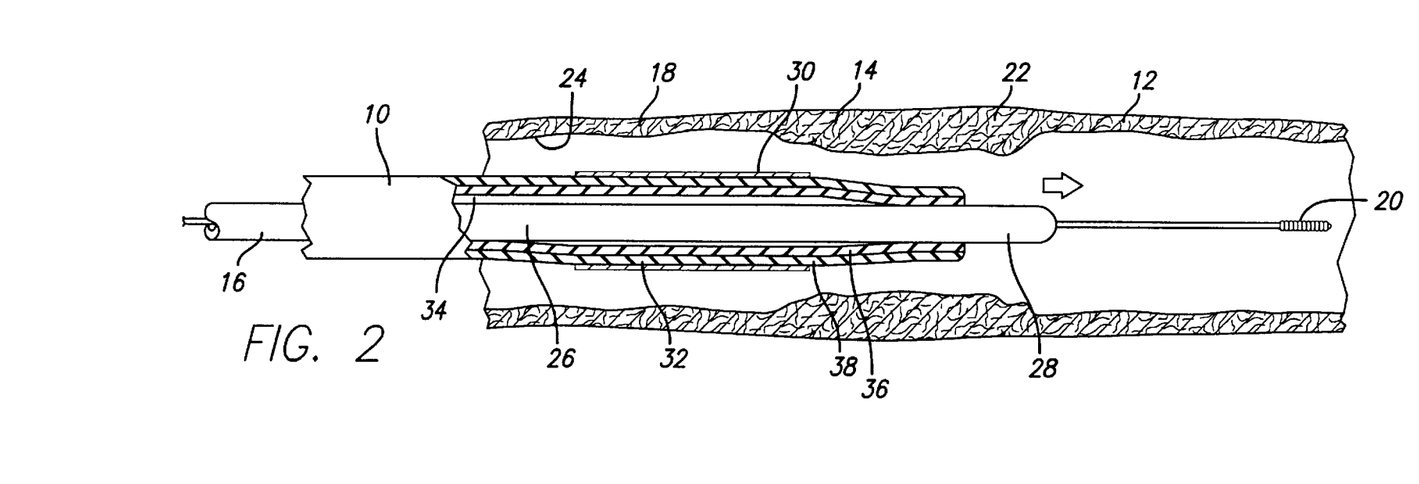
FIG. 2 is an elevational view, partially in section, similar to that shown in FIG. 1, depicting the system of the present invention disposed within the internal carotid artery of a patient, further including an expandable interventional instrument, wherein the expandable member and the expandable interventional instrument in unexpanded condition.

Referring now to the drawings, wherein like reference numerals denote like or corresponding parts throughout the drawing figures, and particularly to FIGS. 1–4, a system 10 is provided for enabling an interventional procedure to be performed in a blood vessel 12 at an area of treatment 14. The system 10 includes a catheter 16 adapted to enable the interventional procedure to be performed. As shown in FIG. 2, the system 10 may be positioned on the catheter 16, and may be placed within the carotid artery 18 or other blood vessel of the patient on the catheter 16 and guided into position by a guide wire 20. The carotid artery 18 may have the area of treatment 14, which may comprise the interventional procedure site, wherein atherosclerotic plaque 22 may have built up against the inside wall 24 which decreases the diameter of the carotid artery 18. As a result, blood flow may be diminished through this area. The catheter 16 may include an elongated shaft 26 having a distal end 28.

The therapeutic interventional procedure may comprise implanting an expandable interventional instrument 30 at the interventional procedure site 14, to compress the build-up of plaque 22 of the stenosis against the inside wall 24, to increase the diameter of the occluded area 14 of the artery 18, and to help restore sufficient flow of blood to the downstream vessels leading to the brain. The expandable interventional instrument 30 not only helps increase the diameter of the occluded area, but may help prevent restenosis in the area of treatment 14. The expandable interventional instrument 30 maybe adapted to be located in the distal end portion 28 of the catheter 16, and to be expanded and deployed at the interventional procedure site 14. It includes an unexpanded axial dimension constituting the unexpanded length thereof, and is adapted to be expandable in a direction generally transverse to the axial dimension thereof. The expandable interventional instrument 30 may comprise for example an expandable stent such as a balloon-expandable stent.

Figure 3:
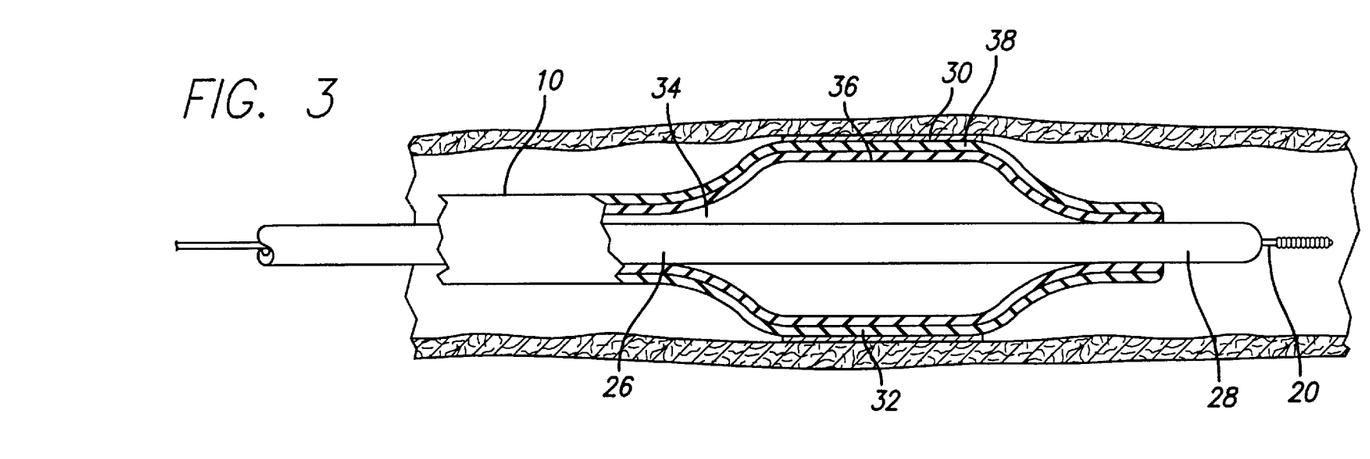
FIG. 3 is an elevational view, partially in section similar to that shown in FIG. 2, wherein the expandable member and the expandable interventional instrument are in expanded condition.
Figure 4:
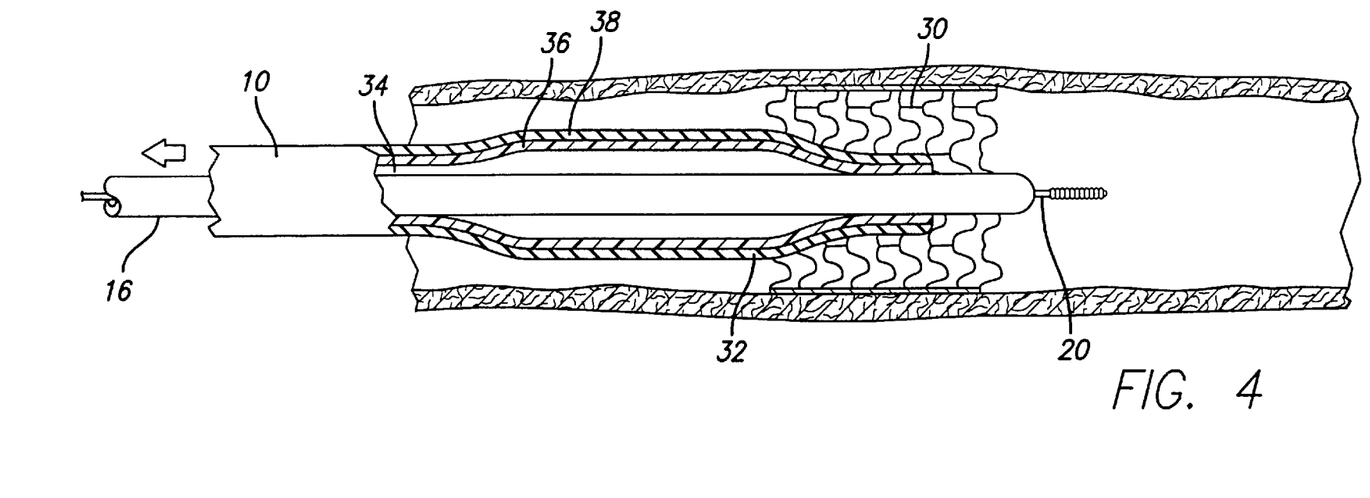
FIG. 4 is an elevational view, partially in section, similar to that shown in FIG. 3, wherein the expanded member is in collapsed condition and the expanded interventional instrument is in expanded condition.

An expandable member 32 for expanding the expandable stent 30 and for enabling the expandable stent 30 to be deployed at the interventional procedure site 14, is adapted to be positioned proximate the distal end 28 of the elongated shaft 26 of the catheter 16, and includes an unexpanded axial dimension. An inflation lumen 34 may extend to the distal end 28 of the elongated catheter shaft 26. The inflation lumen 34 may receive and remove fluid, such as saline or other inflation fluid, for expanding and contracting the expandable member 32. As can be seen in FIGS. 2–3, the expandable member 32 may be expanded in a direction generally transverse to the axial dimension thereof so as to expand and deploy the expandable stent 30 to make full contact with and compress the plaque 22 in the walls 24 of the carotid artery 18.

The expandable member 32 maybe adapted to substantially adhere to the expandable stent 30 so as to be in contact with the expandable stent 30 and provide security for the expandable stent 30, and to substantially retain the unexpanded axial dimensions of the expandable member 32 and the expandable stent 30 upon expansion thereof so as to prevent slippage of the expandable stent during deployment and minimize stent shortening or lengthening. The expandable member 32 may comprise an expandable balloon.

In an embodiment of the invention as shown in FIGS. 1–4, the expandable balloon 32 may be comprised of a plurality of layers, comprising a layer 36 and a layer 38. The layer 36 maybe comprised of a material which has a substantially low axial growth and which is adapted to substantially retain the unexpanded axial dimension of the expandable stent 30 upon expansion of the expandable member 32 and the expandable stent 30. The layer 36 may be comprised of a thermoplastic polyamide such as "Nylon 12", and may comprise the inner layer of the expandable balloon 32, adapted to prevent lengthening or shortening of the expandable stent 30. The layer 38 may be comprised of a material which has a substantially high coefficient of friction and which is adapted to increase the adhesion between the expandable balloon 32 and the expandable stent 30 such that the expandable balloon 32 substantially adheres to the expandable stent 30. The layer 38 may be comprised of an elastomer such as polyurethane, and may comprise the outer layer of the expandable balloon, adapted to provide adhesion to the expandable stent 30.

Figure 5:
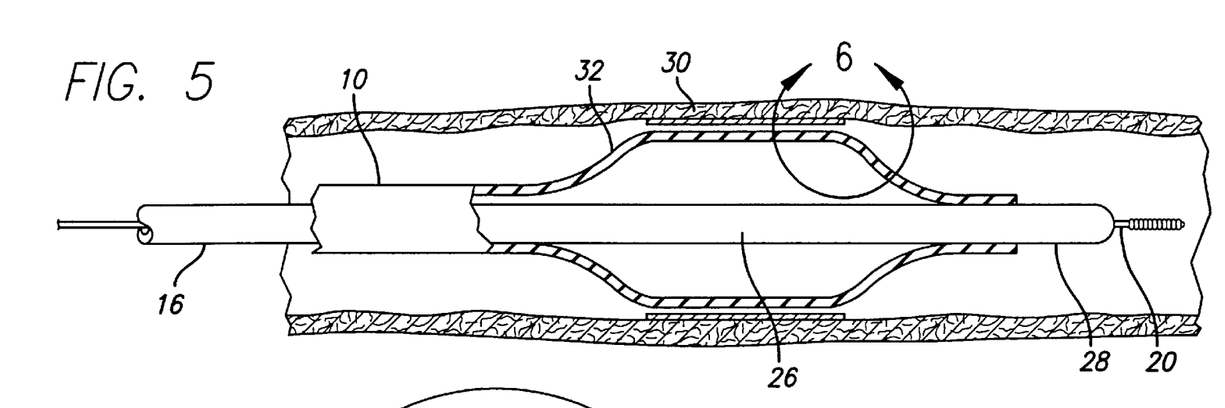
FIG. 5 is an elevational view, partially in section, depicting the system of the present invention disposed within the internal carotid artery of a patient, including a catheter, and a second embodiment of an expandable member and an expandable interventional instrument in expanded condition.
Figure 6:
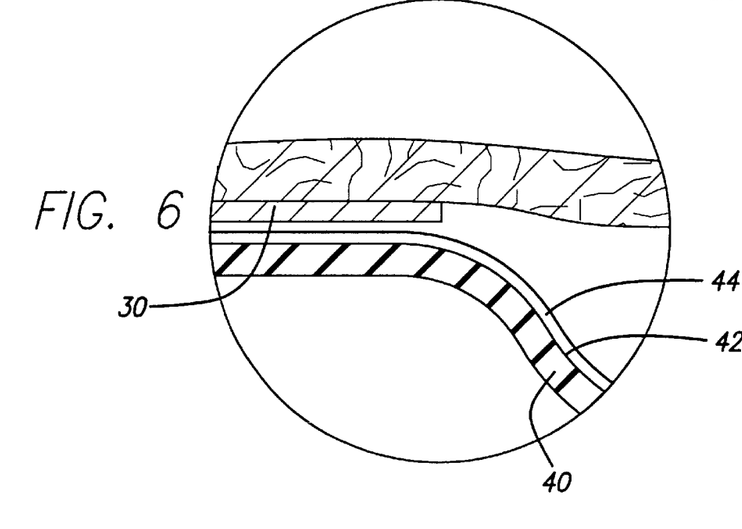
FIG. 6 is an elevational detail of the area encircled in FIG. 5, of a section of the internal carotid artery, the expandable interventional instrument, and the second embodiment of the expandable member.

In another embodiment of the invention as shown in FIGS. 5–6, the expandable balloon 32 may be comprised of a layer 40 including an outer surface 42 and a coating 44. The layer 40 may be comprised of a material which has a substantially low axial growth and which is adapted to substantially retain the unexpanded axial dimension of the expandable stent 30 upon expansion of the expandable member 32 and the expandable stent 30. The layer 40 may be comprised of a thermoplastic polyamide such as "Nylon 12," adapted to prevent lengthening or shortening of the expandable stent 30. The coating 44 maybe comprised of a material which has a substantially high coefficient of friction and which is adapted to increase the adhesion between the expandable balloon 32 and the expandable stent 30 such that the expandable balloon 32 substantially adheres to the expandable stent 30, and may be comprised of an elastomer such as polyurethane, adapted to provide adhesion to the expandable stent 30, and may coat the outer surface 42 of the layer 40.

Materials adapted for use in the layer 36 or the layer 40, for example, may comprise a "Nylon 12" manufactured by EMS-Chemical, Inc. under the trade name "Grilamid L25", a "PET" manufactured by Eastman Chemical Company under the trade name "Eastar", or a "Polyether amide" manufactured by Elf Atochem S.A. under the trade name "Pebax." Materials adapted for use in the layer 38 or the coating 44, for example, may comprise an "SEB" manufactured by Consolidated Polymer Technologies, Inc. under the trade name "C-Flex", or a "polyurethane," manufactured by Dow Chemicals under the trade name "Pellathane", or manufactured by Thermedies, Inc. under the trade name "Tecothane."

In use, as illustrated in FIGS. 1–6, the system 10 may be positioned in the patient's vasculature utilizing any one of a number of different methods. In one preferred method of positioning, the catheter 16 maybe placed in the blood vessel 12 by utilizing the guidewire 20 which is inserted into the patient's vasculature and manipulated by the physician to the area of treatment 14. Thereafter, once the guidewire 20 is in place, the catheter 16 may be maneuvered over the guidewire 20 (via a central lumen) using well-known over-the-wire techniques to place the catheter 16 at a location proximal to the area of treatment 14. After the catheter 16 is in place, the guidewire 20 may be removed from the central lumen by the physician. Once the catheter 16 is in position in the blood vessel 12 with the expandable member 32 at the treatment area 14, the expandable member 32 and the expandable stent 30 of the catheter 16 may be used to contact and pin the plaque 22 at the treatment area 14 by inflating the expandable member 32 through the lumen 34 so as to expand the expandable stent 30. The inflation of the expandable member 32 may be achieved at a proximal end of the elongated shaft 26 of the catheter 16 utilizing a multi-arm adapter which may be attached to an inflation pump or syringe to expand the expandable member 32.

Upon inflation of the expandable member 32, the expandable stent 30 expands into position and compresses the plaque 22 at the area of treatment 14. The expandable stent 30 substantially retains its unexpanded axial dimension upon expansion thereof, so as to treat the entire affected area, without affecting the healthy tissue, responsive to the substantial friction and adhesion of the adhesion layer 38 or the coating 44, and the retention of the retention layer 36 or the layer 40 of the expandable member 32. For example, if the affected area to be treated was 28 mm. in length, and the unexpanded length of the expandable stent 30 was 28 mm., the expandable member 32 herein would substantially retain the 28 mm. length of the expandable stent 30 upon expansion thereof, so as to treat the entire lesion. This would prevent lengthening of the expandable stent 30, for example, to 32 mm. whereby 4 mm. of healthy tissue may be affected, and would also prevent shortening of the expandable stent 30, for example, to 24 mm., whereby 4 mm. of the affect area may be untreated, and it would be difficult to precisely position the expandable stent 30 to treat the affected area.

After the expandable stent 30 is deployed in the treatment area 18, the expandable member 32 may be deflated by removing the fluid therein through the lumen 34. The expansion pressure of the expandable stent 30 upon expansion thereof is greater than the adhesion and friction pressure of the adhesion layer 38 or the coating 44 of the expandable member 32, enabling the expandable member 32 to release from adhesion to the expandable stent 30 and to collapse. Upon the collapse of the expandable member 32, the catheter 16 may be withdrawn, leaving the expandable stent 30 in position in the blood vessel 12. The deflation of the expandable member 32 maybe achieved at the proximal end of the elongated shaft 26 of the catheter 16 utilizing the multi-arm adapter which may be attached to the inflation pump or syringe to deflate the expandable member 32.

In the embodiment of the invention illustrated FIGS. 1–4, as seen in FIG. 2, an interventional device, such as the catheter 16, including the expandable member 32 and the expandable stent 30, may be positioned in the patient's vasculature in the area of treatment 18 utilizing the elongated shaft 26 of the catheter 16 and the guide wire 20, using well-known over-the-wire techniques. Upon positioning the expandable member 32 and the expandable stent 30 at the treatment area 18, the expandable member 32 may be expanded in a direction generally transverse to the axial dimension thereof by receiving fluid through the lumen 34, which expands the expandable stent 30 to compress the build-up of plaque 22 in the treatment area 14. The adhesion outer layer 36 of the expandable member 32, which may be comprised for example of an elastomer such as polyurethane, substantially adheres to the expandable stent 30. The retention inner layer 36 of the expandable member 32, which maybe comprised for example of a thermoplastic polyamide such as "Nylon 12," substantially retains the unexpanded axial dimension of the expandable member 32 and the expandable stent 30, so as to accurately and efficiently compress the extent of the plaque intended to be covered at the area of treatment 14.

In the embodiment of FIGS. 5–6, as shown in FIG. 5, upon positioning the catheter 16 in the blood vessel 12 at the treatment area 14, the expandable member 32 may be inflated for example through infusion of fluid through the lumen 34, whereby the expandable member 32 expands in a direction generally transverse to the axial dimension thereof. The coating 44 on the outer surface 42 of the layer 40, which may be comprised for example of an elastomer such as polyurethane, substantially adheres to the expandable stent 30. The layer 40, which may be comprised for example of a thermoplastic polyamide such as "Nylon 12," substantially retains the unexpanded axial dimension of the expandable member 32 and the expandable stent 30, so as to accurately and efficiently compress the extent of the plaque intended to be covered at the area of treatment 14.

The process of forming the expandable balloon 32 may comprise, for example, blow molding. The process of forming the adhesion coating 44 may comprise, for example, dip molding, spray coating wherein a coating is sprayed on a stationary layer 40, solvent casting wherein a polymer is dissolved to form a low viscosity solution, or spin coating wherein a coating is sprayed on a rotating layer 40. Alternatively, the coating 44 maybe formed, for example, by melting or bonding a soft sheet on the layer 40, of an adhesion material having a durometer in the range of 40$a$–75$d$, at a temperature of about 70 degrees centigrade, or brushing the adhesion material onto the layer 40.

It should be appreciated that the particular embodiments of the expandable member 32 are capable of being positioned in the blood vessel 14. However, other forms of the expandable member 32 may be utilized with the present invention without departing from the spirit and scope of the invention. For example, the expandable member 32 may further be comprised of other forms of material. Additionally, while the expandable member 32 is shown as in various shapes in the embodiments herein, it can be formed in any one of a number of different shapes depending upon the construction desired.

The catheter assembly 16 of the present invention may be formed of conventional materials of construction. The catheter shaft 26 can be made out of relatively inelastic materials such as polyethylene, polyvinyl chloride, polyesters and composite materials. The various components may be joined by suitable adhesives based adhesives or cyanoacrylate based adhesives. Heat shrinking or heat bonding may also be employed where appropriate. Plastic-to-plastic or plastic-to-metal joints can be effected by a suitable acrylonitrile or cyanoacrylate adhesive. Variations can be made in the composition of the materials to vary properties as needed.

In view of the foregoing, it is apparent that the system and method of the present invention enhances substantially the effectiveness of performing interventional procedures by substantially retaining the unexpanded axial dimension of an expandable interventional instrument upon expansion thereof to accurately and effectively pin and compress plaque at the interventional procedure site. Further modifications and improvements may additionally be made to the system and method disclosed herein without the departing from the scope of the invention. Accordingly, it is not intended that the invention be limited, except as by the appended claims.

What is claimed:

1. A system for enabling an interventional procedure to be performed in a blood vessel at an interventional procedure site, comprising:
- a catheter, including an elongated shaft which includes a distal end portion adapted to be positioned in a blood vessel at an interventional procedure site;
- an expandable interventional instrument, adapted to be located in the distal end portion of the catheter shaft, and to be expanded and deployed in the blood vessel at the interventional procedure site, which expandable interventional instrument includes an unexpanded axial dimension, and is adapted to be expandable in a direction generally transverse to the axial dimension thereof; and
- an expansion enabling element for enabling the expansion of the expandable interventional instrument, adapted to be located in the distal end portion of the catheter shaft, to be expandable within the blood vessel at the interventional procedure site in a direction generally transverse to the axial dimension thereof, to substantially adhere to the expandable interventional instrument, and to substantially retain the unexpanded axial dimension of the expandable interventional instrument upon expansion thereof, comprising a plurality of layers, including a retaining layer for substantially retaining the unexpanded axial dimension of the expandable interventional instrument upon expansion of the expansion enabling element.

2. The system of claim 1, wherein the plurality of layers further includes an adhering layer for substantially adhering to the expandable interventional instrument.

3. The system of claim 2, wherein the adhering layer is comprised of an elastomer.

4. The system of claim 3, wherein the elastomer comprises polyurethane.

5. The system of claim 2, wherein the adhering layer comprises an outer layer of the expandable member.

6. The system of claim 2, wherein the retaining layer comprises an inner layer which is not exposed to the exterior upon expansion of the expansion enabling element.

7. The system of claim 1, wherein the retaining layer is comprised of a thermoplastic polyamide.

8. The system of claim 7, wherein the thermoplastic polyamide comprises Nylon 12.

9. The system of claim 1, wherein the retaining layer comprises an inner layer of the expandable member.

10. The system of claim 1, wherein the expansion enabling element comprises an expandable member.

11. The system of claim 1, wherein the expandable interventional instrument comprises an expandable stent.

12. The system of claim 11, wherein the expandable stent comprises a balloon-expandable stent.

13. A system for enabling an interventional procedure to be performed in a blood vessel at an interventional procedure site, comprising:
- a catheter, including an elongated shaft which includes a distal end portion adapted to be positioned in a blood vessel at an interventional procedure site;
- an expandable interventional instrument, adapted to be located in the distal end portion of the catheter shaft, and to be expanded and deployed in the blood vessel at the interventional procedure site, which expandable interventional instrument includes an unexpanded axial dimension, and is adapted to be expandable in a direction generally transverse to the axial dimension thereof; and
- an expandable member for expanding the expandable interventional instrument, adapted to be located in the distal end portion of the catheter shaft, to be expandable within the blood vessel at the interventional procedure site in a direction generally transverse to the axial dimension thereof, to substantially adhere to the expandable interventional instrument, and to substantially retain the unexpanded axial dimension of the expandable interventional instrument upon expansion thereof, comprising a retaining layer for substantially retaining the unexpanded axial dimension of the expandable interventional instrument upon expansion of the expansion enabling element.

14. The system of claim 13, wherein the expandable member further comprises an adhering coating for substantially covering the retaining layer and substantially adhering to the expandable interventional instrument.

15. The system of claim 14, wherein the adhering coating comprises an elastomer.

16. The system of claim 13, wherein the retaining layer is comprised of a thermoplastic polyamide.

17. The system of claim 16, wherein the thermoplastic polyamide comprises Nylon 12.

18. The system of claim 13, wherein the expandable member comprises an expandable balloon.

19. The system of claim 13, wherein the expandable interventional instrument comprises an expandable stent.

20. The system of claim 19, wherein the expandable stent comprises a balloon-expandable stent.

21. A system for enabling an interventional procedure to be performed in a blood vessel at an interventional procedure site, comprising:
- a catheter, including an elongated shaft which includes a distal end portion adapted to be positioned in a blood vessel at an interventional procedure site;
- an expandable interventional instrument, adapted to be located in the distal end portion of the catheter shaft, and to be expanded and deployed in the blood vessel at the interventional procedure site, which expandable interventional instrument includes an unexpanded axial dimension, and is adapted to be expandable in a direction generally transverse to the axial dimension thereof; and
- means for expanding the expandable interventional instrument, adapted to be located in the distal end portion of the catheter shaft, to be expandable within the blood vessel at the interventional procedure site in a direction generally transverse to the axial dimension thereof, to substantially adhere to the expandable interventional instrument, and to substantially retain the unexpanded axial dimension of the expandable interventional instrument upon expansion thereof, comprising a plurality of layers, including a retaining layer for substantially retaining the unexpanded axial dimension of the expandable interventional instrument upon expansion of the expansion enabling element.

22. The system of claim 21, wherein the plurality of layers of the expanding means further includes an adhering layer for substantially adhering to the expandable interventional instrument.

23. A system for enabling an interventional procedure to be performed in a blood vessel at an interventional procedure site, comprising:

a catheter, including an elongated shaft which includes a distal end portion adapted to be positioned in a blood vessel at an interventional procedure site:

an expandable interventional instrument, adapted to be located in the distal end portion of the catheter shaft, and to be expanded and deployed in the blood vessel at the interventional procedure site, which expandable interventional instrument includes an unexpanded axial dimension, and is adapted to be expandable in a direction generally transverse to the axial dimension thereof; and means for expanding the expandable interventional instrument, adapted to be located in the distal end portion of the catheter shaft, to be expandable within the blood vessel at the interventional procedure site in a direction generally transverse to the axial dimension thereof, to substantially adhere to the expandable interventional instrument, and to substantially retain the unexpanded axial dimension of the expandable interventional instrument upon expansion thereof, comprising a retaining layer for substantially retaining the unexpanded axial dimension of the expandable interventional instrument upon expansion of the expansion enabling element.

24. The system of claim 23, wherein the expanding means further comprise an adhering coating for substantially covering the retaining layer and substantially adhering to the expandable interventional instrument.

25. A method of enabling an interventional procedure to be performed in a blood vessel at an interventional procedure site, in a system which comprises a catheter, including an elongated shaft which includes a distal end portion adapted to be positioned in a blood vessel at an interventional procedure site, an expandable interventional instrument, adapted to be located in the distal end portion of the catheter, and to be expanded and deployed in the blood vessel at the interventional procedure site, which expandable interventional instrument includes an unexpanded axial dimension, and is adapted to be expandable in a direction generally transverse to the axial dimension thereof, and an expandable member for expanding the expandable interventional instrument, adapted to be located in the distal end portion of the catheter shaft, to be expandable within the blood vessel at the interventional procedure site in a direction generally transverse to the axial dimension thereof, to substantially adhere to the expandable interventional instrument, and to substantially retain the unexpanded axial dimension of the expandable interventional instrument upon expansion thereof, comprising a plurality of layers, including a retaining layer for substantially retaining the unexpanded axial dimension of the expandable interventional instrument upon expansion of the expansion enabling element, wherein the method comprises:

substantially adhering the expandable member to the expandable interventional instrument; and expanding the expandable member so as to substantially adhere to and expand the expandable interventional instrument and to substantially retain the unexpanded axial dimension of the expandable interventional instrument upon expansion of the expandable member and the expandable interventional instrument.

26. The method of claim 25, wherein the plurality of layers further includes an adhering layer for substantially adhering to the expandable interventional instrument, and expanding further comprises expanding the adhesion layer.

27. A method of enabling an interventional procedure to be performed in a blood vessel at an interventional procedure site, in a system which comprises a catheter, including an elongated shaft which includes a distal end portion adapted to be positioned in a blood vessel at an interventional procedure site, an expandable interventional instrument, adapted to be located in the distal end portion of the catheter shaft, and to be expanded and deployed in the blood vessel at the interventional procedure site, which expandable interventional instrument includes an unexpanded axial dimension, and is adapted to be expandable in a direction generally transverse to the axial dimension thereof, and an expansion enabling an element for enabling the expansion of the expandable interventional instrument, comprising an expandable member adapted to be located in the distal end portion of the catheter shaft, to be expandable within the blood vessel at the interventional procedure site in a direction generally transverse to the axial dimension thereof, to substantially adhere to the expandable interventional instrument, and to substantially retain the unexpanded axial dimension of the expandable interventional instrument upon expansion thereof, comprising a retaining layer for substantially retaining the unexpanded axial dimension of the expandable interventional instrument upon expansion of the expandable member and the expandable interventional instrument, wherein the method comprises:

substantially adhering the expandable member to the expandable interventional instrument; and expanding the expandable member so as to substantially adhere to and expand the expandable interventional instrument and to substantially retain the unexpanded axial dimension of the expandable interventional instrument upon expansion of the expandable member and the expandable interventional instrument.

28. The method of claim 27, wherein the expandable member further comprises an adhering coating for substantially covering the outer surface of the outer surface of the layer and substantially adhering to the expandable interventional instrument, and substantially adhering further comprises substantially adhering the coating to the expandable interventional instrument.

* * * * *

UNITED STATES PATENT AND TRADEMARK OFFICE
CERTIFICATE OF CORRECTION

PATENT NO.    : 6,506,202 B1
DATED         : January 14, 2003
INVENTOR(S)   : Debashis Dutta et al.

It is certified that error appears in the above-identified patent and that said Letters Patent is hereby corrected as shown below:

<u>Column 8,</u>
Line 5, change "36", to read -- 38 --.

Signed and Sealed this

Twenty-fourth Day of June, 2003

JAMES E. ROGAN
*Director of the United States Patent and Trademark Office*